(12) United States Patent
Osaka

(10) Patent No.: US 8,283,855 B2
(45) Date of Patent: Oct. 9, 2012

(54) METHOD FOR SYNTHESIS OF ANTHRACENE DERIVATIVE

(75) Inventor: Harue Osaka, Sagamihara (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 19 days.

(21) Appl. No.: 12/985,370

(22) Filed: Jan. 6, 2011

(65) Prior Publication Data

US 2011/0172441 A1 Jul. 14, 2011

(30) Foreign Application Priority Data

Jan. 11, 2010 (JP) ................................. 2010-003487

(51) Int. Cl.
- C08G 73/06 (2006.01)
- H01L 51/42 (2006.01)
- H05B 33/14 (2006.01)

(52) U.S. Cl. ........ 313/504; 313/506; 428/690; 428/704; 428/917; 528/423

(58) Field of Classification Search .................. 313/504, 313/506; 428/690, 704, 917; 528/423
See application file for complete search history.

(56) References Cited

U.S. PATENT DOCUMENTS

| | | | |
|---|---|---|---|
| 7,505,122 B2 * | 3/2009 | Nomura et al. ................. | 356/32 |
| 7,541,098 B2 | 6/2009 | Nomura et al. | |
| 7,646,010 B2 | 1/2010 | Kawakami et al. | |
| 7,674,914 B2 | 3/2010 | Egawa et al. | |
| 7,723,722 B2 | 5/2010 | Kawakami et al. | |
| 7,732,064 B2 | 6/2010 | Kawakami et al. | |
| 7,838,128 B2 | 11/2010 | Kawakami et al. | |
| 7,842,945 B2 | 11/2010 | Egawa et al. | |
| 2006/0292394 A1 | 12/2006 | Iwaki et al. | |
| 2007/0049778 A1 | 3/2007 | Nomura et al. | |
| 2007/0075632 A1 | 4/2007 | Kawakami et al. | |
| 2007/0267969 A1 | 11/2007 | Nakashima et al. | |
| 2008/0086012 A1 | 4/2008 | Egawa et al. | |
| 2008/0107918 A1 | 5/2008 | Egawa et al. | |
| 2008/0268284 A1 | 10/2008 | Kawakami et al. | |
| 2008/0286445 A1 | 11/2008 | Suzuki et al. | |
| 2009/0004506 A1 | 1/2009 | Nomura et al. | |
| 2009/0015140 A1 | 1/2009 | Kawakami et al. | |
| 2009/0026922 A1 | 1/2009 | Iwaki et al. | |
| 2009/0058278 A1 | 3/2009 | Ushikubo et al. | |
| 2009/0102360 A1 | 4/2009 | Kawakami et al. | |
| 2009/0174321 A1 | 7/2009 | Osaka et al. | |
| 2009/0236590 A1 | 9/2009 | Ohsawa | |
| 2009/0247795 A1 | 10/2009 | Kawakami | |
| 2009/0253916 A1 | 10/2009 | Kawakami et al. | |
| 2009/0267497 A1 | 10/2009 | Kawakami et al. | |
| 2009/0267498 A1 | 10/2009 | Kawakami et al. | |
| 2009/0317539 A1 | 12/2009 | Shitagaki et al. | |
| 2009/0322211 A1 | 12/2009 | Takahashi et al. | |
| 2010/0051926 A1 | 3/2010 | Kawakami et al. | |
| 2010/0069647 A1 | 3/2010 | Suzuki et al. | |
| 2010/0076201 A1 | 3/2010 | Suzuki et al. | |
| 2010/0096981 A1 | 4/2010 | Seo et al. | |
| 2010/0099890 A1 | 4/2010 | Ogita et al. | |
| 2010/0148166 A1 | 6/2010 | Ushikubo et al. | |
| 2010/0156957 A1 | 6/2010 | Ogita et al. | |

FOREIGN PATENT DOCUMENTS

JP 2009-167175 A 7/2009

* cited by examiner

*Primary Examiner* — Susannah Chung
(74) *Attorney, Agent, or Firm* — Eric J. Robinson; Robinson Intellectual Property Law Office, P.C.

(57) ABSTRACT

A method for synthesizing an anthracene derivative represented by a general formula (G1) is provided, in which a 9-arylanthracene derivative having an active site at a 10-position is subjected to coupling with a carbazole-3-yl-aryl derivative having an active site in an aryl group with the use of a metal or a metal compound, wherein A represents a substituted or unsubstituted phenyl group, wherein D represents any of an alkyl group having 1 to 4 carbon atoms and a substituted or unsubstituted phenyl group, wherein α represents any of a substituted or unsubstituted phenylene group and a substituted or unsubstituted biphenyl-4,4'-diyl group, and wherein $R^1$ to $R^9$ independently represent any of hydrogen, an alkyl group having 1 to 4 carbon atoms, and a substituted or unsubstituted phenyl group.

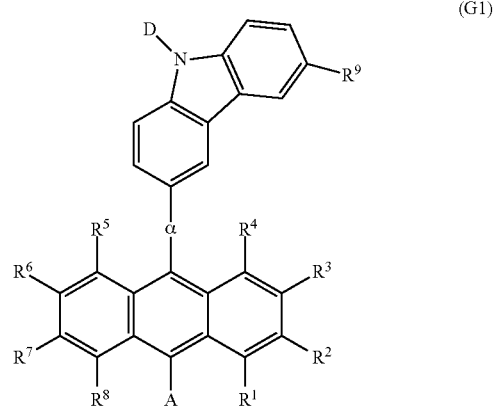

(G1)

9 Claims, 3 Drawing Sheets

METHOD FOR SYNTHESIS OF ANTHRACENE DERIVATIVE

BACKGROUND OF THE INVENTION

1. Field of the Invention

The present invention relates to a method for synthesizing an anthracene derivative.

2. Description of the Related Art

In recent years, research and development of light-emitting elements using electroluminescence (EL) have been actively carried out. In a basic structure for these light-emitting elements, a layer containing a luminescent substance is interposed between a pair of electrodes. By applying a voltage to this element, luminescence can be obtained from the luminescent substance.

Such light-emitting elements are classified into a self-luminous type, and thus have advantages such as higher pixel visibility and the eliminated need for a backlight, as compared with liquid crystal displays. Accordingly, such light-emitting elements are thought to be suitable as flat panel display elements. In addition, such light-emitting elements also have the great advantage of being able to be manufactured to have thinness and lightness. Furthermore, it is also one of the features of such light-emitting elements that the response speed is very high.

Furthermore, since these light-emitting elements can be formed in the form of a film, planar light emission can be obtained. Therefore, large-area elements can be easily formed. This is a feature which is difficult to obtain from point light sources typified by an incandescent lamp and an LED or linear light sources typified by a fluorescent lamp. Accordingly, the light-emitting elements using EL have a great deal of potential for use as planar light sources which can be applied to illumination and the like.

The light-emitting elements using electroluminescence can be roughly classified in accordance with whether the luminescent substance is an organic compound or an inorganic compound. In the case of an organic EL element in which an organic compound is used for the luminescent substance to provide a layer containing the luminescent organic compound between a pair of electrodes, when a voltage is applied to the light-emitting element, electrons and holes are respectively injected from a cathode and an anode into the layer containing the luminescent organic compound, thereby allowing a current to flow. Then, the injected electrons and holes bring the luminescent organic compound into an excited state, in such a way that luminescence is obtained from the excited luminescent organic compound.

On the basis of such a mechanism, the above-described light-emitting element is referred to as a current-excitation type light-emitting element. It is to be noted that the excited states formed by an organic compound include a singlet excited state and a triplet excited state, and luminescence from the singlet excited state is referred to as fluorescence, whereas luminescence from the triplet excited state is referred to as phosphorescence.

In addition to luminescence through recombination of carriers excited by a current, there is also a method in which the excitation energy of an organic compound excited by a current is transferred to another organic compound, thereby exciting the latter organic compound to produce luminescence. This method is effective in the case of the luminance efficiency reduced (concentration quenching) due to stacking interaction caused by a high concentration of organic molecules that are desired to produce luminescence. In organic EL elements, the method is generally applied to the element structure used in which a luminescent material is dispersed in a light-emitting layer (a light-emitting layer is doped with a luminescent material). Doping a host material with organic molecules that are desired to produce luminescence suppresses the stacking interaction, thereby allowing the efficiency of the light-emitting element to be increased. In such a light-emitting element, the excitation energy is transferred from a host material excited by current excitation to a dopant material, thereby allowing the dopant material to produce luminescence. It is to be noted that when a substance A is dispersed in a matrix composed of a substance B, the substance B constituting the matrix is referred to as a host material, whereas the substance A dispersed in the matrix is referred to as a dopant material.

While various analyses have been carried out in regard to the deterioration mechanism of light-emitting elements, the mechanism has not been fully determined yet actually. It is believed that the deterioration mechanism involves various factors, and the purity of an organic material for use in light-emitting elements can be cited as one of the factor. As for a light-emitting element, it is known that if an inorganic metal compound is adjacent to a light-emitting site of the light-emitting element, the light-emitting site is changed to a quenching site, which results in one of the factors that the efficiency of the element is decreased or that the element is deteriorated. Therefore, low molecular weight organic materials for organic EL elements are typically purified before use by a method such as sublimation to increase the degree of purity, in addition to common methods for purification of organic matters. However, in regard to the deterioration factors caused by the other impurities, it has not been clear yet which factor is involved in deterioration. Therefore, in order to clarify the deterioration factors as much as possible, it has been desired to obtain materials including fewer impurities.

Furthermore, in general, it is desirable in regard to the synthesis of organic compounds to obtain intended products with a higher degree of purity in a simple manner, and various methods have been thus made. The means for obtaining intended products with a higher degree of purity in a simple manner include the adoption of a synthesis root using more stable raw materials which are easily purified and the adoption of a synthesis root which is less likely to synthesize by-products. As described above, efforts have been made such that the lot-to-lot variation in material can be further reduced. When materials with reduced lot-to-lot variation in material are adopted for devices such a light-emitting elements, characteristics with less variation can be obtained.

In addition, while organic compounds are able to be synthesized in a variety of ways, the synthesis often involves multiple synthesis steps. Therefore, the more complex the synthesis method is, the more raw materials and time are consumed. Accordingly, the proposal of simpler synthesis methods has been desired.

One of organic materials for use in light-emitting elements is 9-phenyl-3-[4-(10-phenyl-9-anthryl)phenyl]-9H-carbazole (abbreviation: PCzPA) (Patent Document 1). This material is a material which is stable against the repetition of reduction and oxidation states (the repetition of from the oxidation state to the reduction state and from the reduction state to the oxidation state), and in particular, can be preferably used as a hole injection layer, a hole transport layer, and a light-emitting layer (a host or a dopant, a luminescent material). However, the method for synthesizing an anthracene derivative such as PCzPA, described in Patent Document 1, has difficulty in removal of a by-product which is likely to be produced in the process. Therefore, if this material can be produced with a high degree of purity and with less variation in a simple manner, more desirable characteristics are obtained stably in light-emitting elements, etc.

REFERENCE

Japanese Patent Application Laid-Open No. 2009-167175

SUMMARY OF THE INVENTION

The present invention has been made in view of above the problems, and it is an object of an aspect of the present invention is to provide a method for synthesizing an anthracene derivative with a high degree of purity in a simpler manner.

An aspect of the present invention is a method for synthesizing an anthracene derivative represented by a general formula (G1), in which a 9-arylanthracene derivative having an active site at a 10-position is subjected to coupling with a carbazole-3-yl-aryl derivative having an active site in an aryl group with the use of a metal or a metal compound.

[Formula 1]

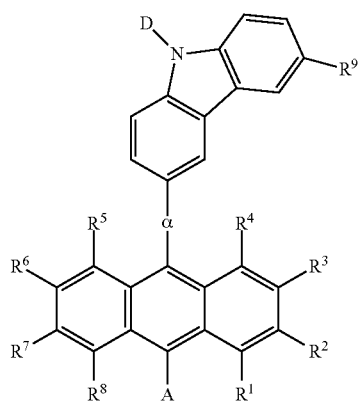

(G1)

In the general formula (G1), A represents a substituted or unsubstituted phenyl group. In addition, D represents any of an alkyl group having 1 to 4 carbon atoms and a substituted or unsubstituted phenyl group. In addition, a represents any of a substituted or unsubstituted phenylene group and a substituted or unsubstituted biphenyl-4,4'-diyl group. In addition, $R^1$ to $R^9$ independently represent any of hydrogen, an alkyl group having 1 to 4 carbon atoms, and a substituted or unsubstituted phenyl group.

In addition, in the method for synthesizing an anthracene derivative, it is preferable that one of the active sites be halogen, whereas the other is a boronic acid or organoboron.

In addition, in the method for synthesizing an anthracene derivative, it is more preferable that the 9-arylanthracene derivative having an active site at a 10-position more have an active site of halogen, whereas the carbazole-3-yl-aryl derivative having an active site in an aryl group more preferably has an active site of a boronic acid or organoboron. This is because the reactivity of the anthracene with a boron compound is favorable when the anthracene has halogen at the 10-position.

In addition, another aspect of the present invention is a method for synthesizing an anthracene derivative represented by a general formula (G1), in which a 9-aryl-10-halogenated anthracene is subjected to coupling with a (9-aryl-9H-carbazol-3-yl)aryl boronic acid with the use of a metal compound.

[Formula 2]

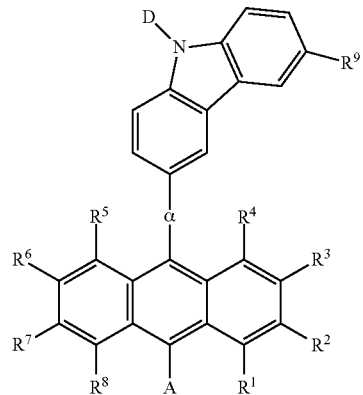

(G1)

In the general formula (G1), A represents a substituted or unsubstituted phenyl group. In addition, D represents any of an alkyl group having 1 to 4 carbon atoms and a substituted or unsubstituted phenyl group. In addition, a represents any of a substituted or unsubstituted phenylene group and a substituted or unsubstituted biphenyl-4,4'-diyl group. In addition, $R^1$ to $R^9$ independently represent any of hydrogen, an alkyl group having 1 to 4 carbon atoms and a substituted or unsubstituted phenyl group.

In addition, another aspect of the present invention is a method for synthesizing an anthracene derivative represented by the general formula (G1), in which an anthracene derivative represented by a general formula (a1) is subjected to coupling with a carbazole derivative represented by a general formula (c3) with the use of a metal or a metal compound.

[Formula 3]

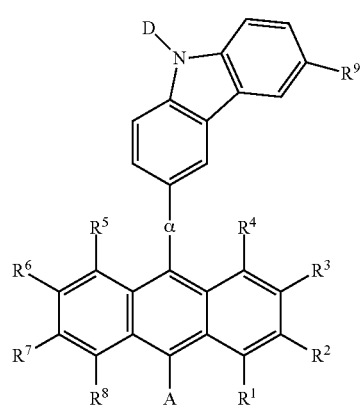

(G1)

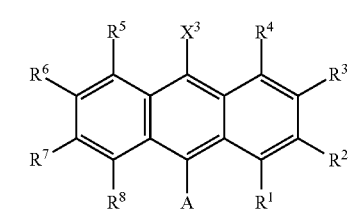

(a1)

(c3)

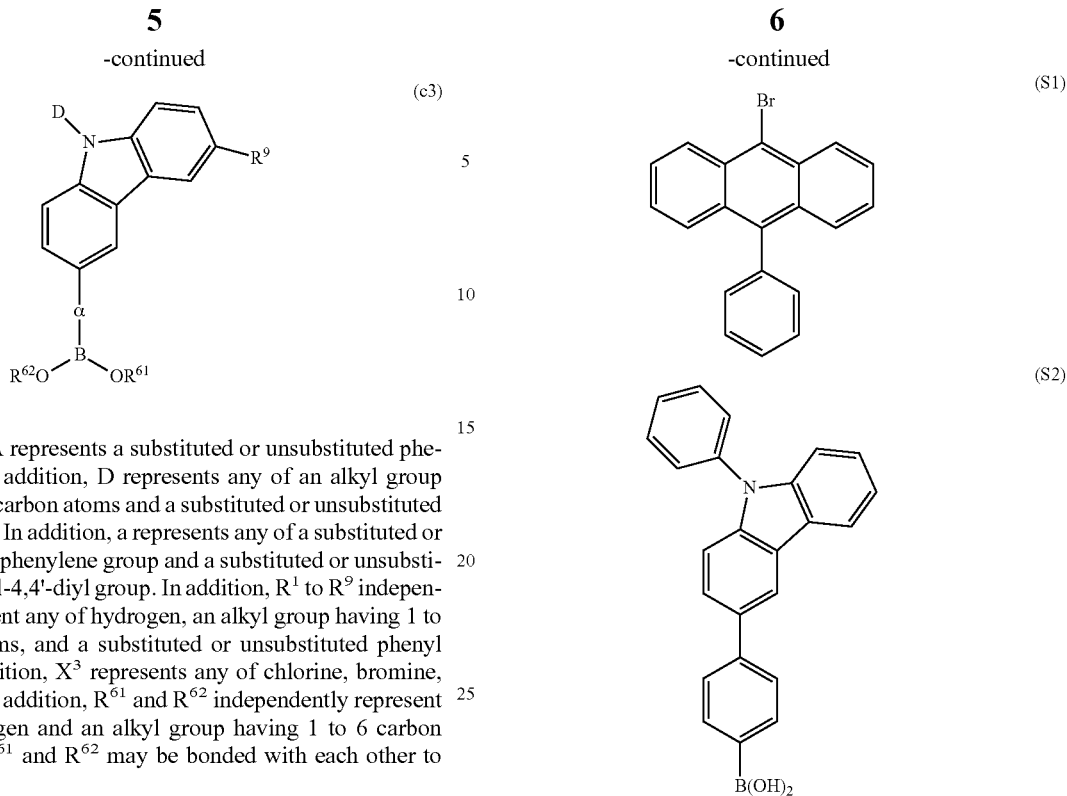

However, A represents a substituted or unsubstituted phenyl group. In addition, D represents any of an alkyl group having 1 to 4 carbon atoms and a substituted or unsubstituted phenyl group. In addition, a represents any of a substituted or unsubstituted phenylene group and a substituted or unsubstituted biphenyl-4,4'-diyl group. In addition, $R^1$ to $R^9$ independently represent any of hydrogen, an alkyl group having 1 to 4 carbon atoms, and a substituted or unsubstituted phenyl group. In addition, $X^3$ represents any of chlorine, bromine, and iodine. In addition, $R^{61}$ and $R^{62}$ independently represent any of hydrogen and an alkyl group having 1 to 6 carbon atoms, and $R^{61}$ and $R^{62}$ may be bonded with each other to form a ring.

In addition, another aspect of the present invention is a method for synthesizing an anthracene derivative represented by the structural formula (P1), in which an anthracene derivative represented by a structural formula (S1) is subjected to coupling with a carbazole derivative represented by a structural formula (S2) with the use of a metal or a metal compound.

[Formula 4]

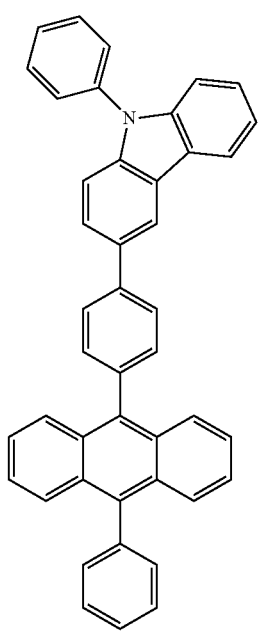

(P1)

In addition, in the method for synthesizing an anthracene derivative, examples of the metal compound include, for example, palladium compounds.

EFFECT OF THE INVENTION

An aspect of the present invention can provide a method for synthesizing an anthracene derivative with a high degree of purity in a simpler manner.

BRIEF DESCRIPTION OF THE DRAWINGS

In the accompanying drawings.

DETAILED DESCRIPTION OF THE INVENTION

Figure 1A:
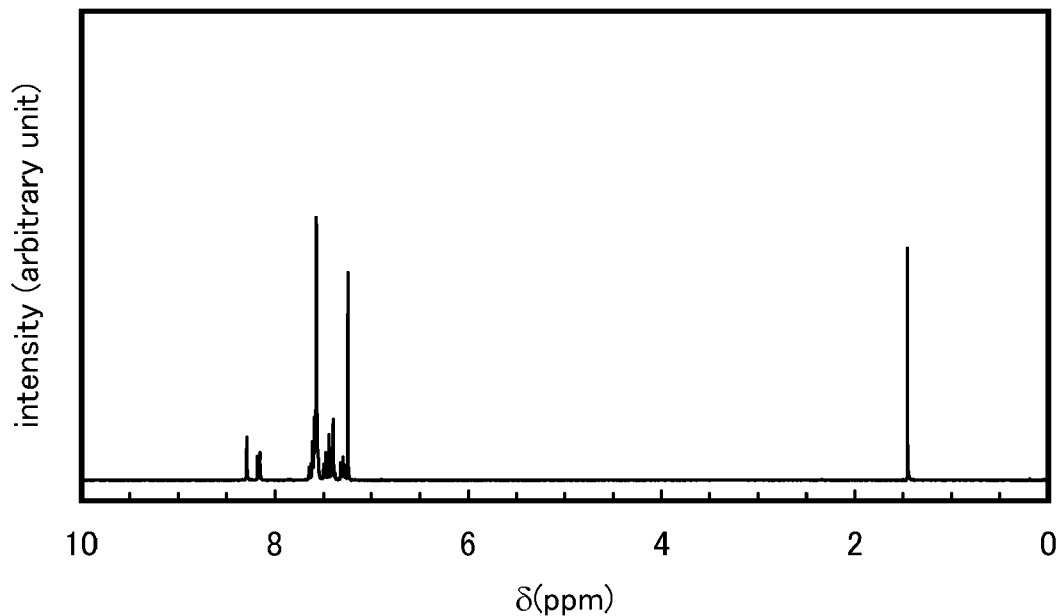
FIGS. 1A and 1B are diagrams showing $^1$H NMR charts for 3-(4-bromophenyl)-9-phenyl-9H-carbazol.

Hereinafter, embodiment modes of the present invention will be described in detail. It is to be noted that the invention is not limited to the following description, and it will be easily understood by those skilled in the art that various changes and modifications can be made without departing from the spirit and scope of the invention. Therefore, the invention should not be construed as being limited to the description in the following embodiments.

Embodiment 1

In this embodiment, a method for synthesizing an anthracene derivative according to an aspect of the present invention will be described.

An aspect of the present invention is a method for synthesizing an anthracene derivative represented by a general formula (G1), in which a 9-arylanthracene derivative having an active site at a 10-position is subjected to coupling with a carbazole-3-yl-aryl derivative having an active site in an aryl group with the use of a metal or a metal compound.

[Formula 5]

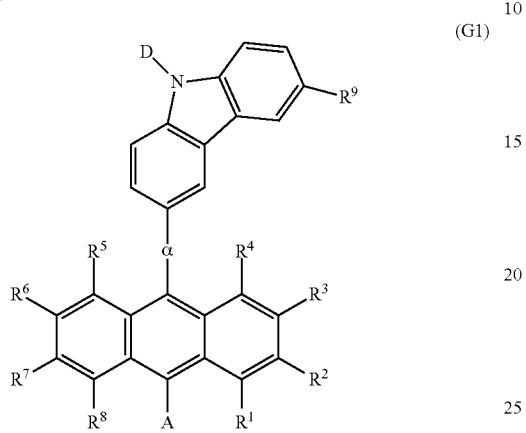

(G1)

In the general formula (G1), A represents a substituted or unsubstituted phenyl group. In addition, D represents any of an alkyl group having 1 to 4 carbon atoms and a substituted or unsubstituted phenyl group. In addition, a represents any of a substituted or unsubstituted phenylene group and a substituted or unsubstituted biphenyl-4,4'-diyl group. In addition, $R^1$ to $R^9$ independently represent any of hydrogen, an alkyl group having 1 to 4 carbon atoms, and a substituted or unsubstituted phenyl group.

In the general formula (G1), when A has a substituent, it is preferable that the substituent be an alkyl group having 1 to 4 carbon atoms or an alkoxy group having 1 to 4 carbon atoms. Examples of the alkyl group having 1 to 4 carbon atoms include, for example, a methyl group, an ethyl group, and a butyl group. Examples of the alkoxy group having 1 to 4 carbon atoms include, for example, a methoxy group, an ethoxy group, and a butoxy group.

Specific structures of A in the general formula (G1) include substituents represented by the structural formulae (10-1) to (10-8).

[Formula 6]

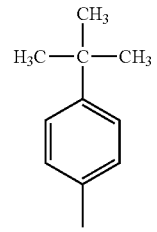

(10-1)

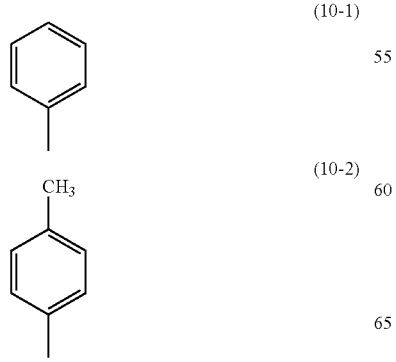

(10-2)

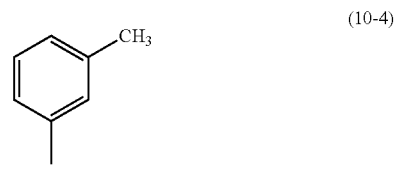

(10-3)

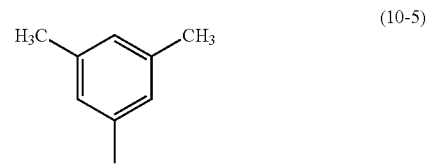

(10-4)

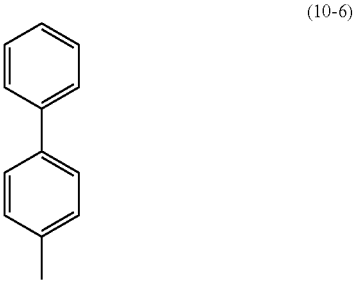

(10-5)

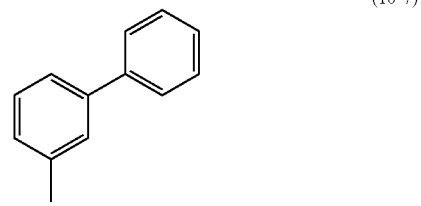

(10-6)

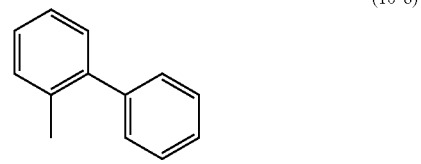

(10-7)

(10-8)

In addition, in the general formula (G1), when a has a substituent, it is preferable that the substituent be an alkyl group having 1 to 4 carbon atoms or an alkoxy group having 1 to 4 carbon atoms. Examples of the alkyl group having 1 to 4 carbon atoms include, for example, a methyl group, an ethyl group, and a butyl group. Examples of the alkoxy group having 1 to 4 carbon atoms include, for example, a methoxy group, an ethoxy group, and a butoxy group.

Specific structures of a in the general formula (G1) include substituents represented by the structural formulae (11-1) to (11-5).

[Formula 7]

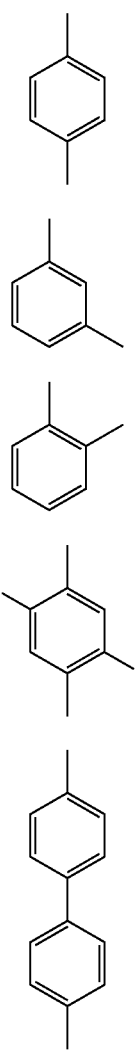

(11-1)
(11-2)
(11-3)
(11-4)
(11-5)

In the general formula (G1), when D has a substituent, it is preferable that the substituent be an alkyl group having 1 to 4 carbon atoms or an alkoxy group having 1 to 4 carbon atoms. Examples of the alkyl group having 1 to 4 carbon atoms include, for example, a methyl group, an ethyl group, and a butyl group. Examples of the alkoxy group having 1 to 4 carbon atoms include, for example, a methoxy group, an ethoxy group, and a butoxy group.

Specific structures of D in the general formula (G1) include substituents represented by the structural formulae (12-1) to (12-12).

[Formula 8]

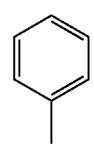 (12-1)

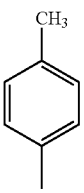 (12-2)

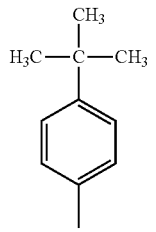 (12-3)

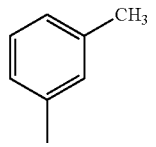 (12-4)

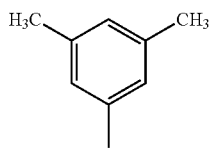 (12-5)

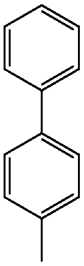 (12-6)

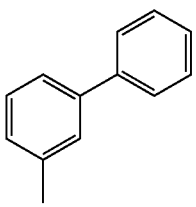 (12-7)

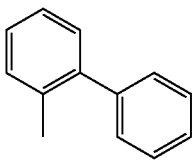 (12-8)

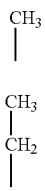 (12-9)

 (12-10)

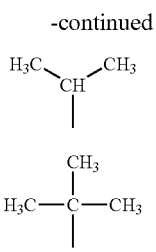

(12-11)

(12-12)

In the general formula (G1), when $R^1$ to $R^9$ have a substituent, it is preferable that the substituent be an alkyl group having 1 to 4 carbon atoms or an alkoxy group having 1 to 4 carbon atoms. Examples of the alkyl group having 1 to 4 carbon atoms include, for example, a methyl group, an ethyl group, and a butyl group. Examples of the alkoxy group having 1 to 4 carbon atoms include, for example, a methoxy group, an ethoxy group, and a butoxy group.

Further, an alkyl group is preferably used as a substituent in the general formula (G1), because the use of the alkyl group improves the solubility in an organic solvent, and thus facilitates purification. In addition, the improvement of the solubility also improves the uniformity of a formed film in the case of manufacturing an organic EL element in accordance with a wet process. Moreover, the use of the alkyl group is preferable, because the molecules form a more three-dimensional structure, which leads to improved film quality and makes it easier to suppress concentration quenching and excimer formation. In addition, examples of the substituent D and of the alkyl group having 1 to 4 carbon atoms in $R^1$ to $R^9$ include a methyl group, an ethyl group, a propyl group, and a butyl group.

In addition, examples of the 9-arylanthracene derivative having an active site at a 10-position, which can be used for the method for synthesizing an anthracene derivative according to an aspect of the present invention, include anthracene derivatives represented by the general formula (a1). However, it is to be noted that the present invention is not limited to these anthracene derivatives.

[Formula 9]

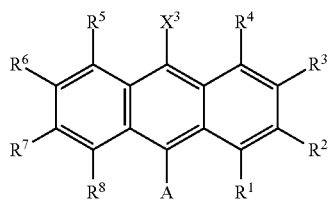

(a1)

In the general formula (a1), A represents a substituted or unsubstituted phenyl group. $R^1$ to $R^8$ independently represent any of hydrogen, an alkyl group having 1 to 4 carbon atoms and a substituted or unsubstituted phenyl group. Furthermore, $X^3$ represents any of chlorine, bromine, and iodine.

$X^3$ in the general formula (a1) is preferably iodine, bromine, or chlorine in this order in consideration of high reactivity with the general formula (c3) described later. In addition, in the case of obtaining a compound with iodine, it is necessary to form a product with iodine in accordance with a halogen substitution reaction after a compound with bromine is formed once, thereby resulting in an increase in the number of synthetic steps. Thus, in consideration of productivity, $X^3$ is preferably bromine or chlorine. Moreover, in consideration of cost, $X^3$ is preferably chlorine which allows reduction in cost.

In addition, specific examples of the 9-arylanthracene derivative having an active site at a 10-position, represented by the general formula (a1), include anthracene derivatives represented by the structural formulae (100) to (124). However, it is to be noted that the present invention is not limited to these anthracene derivatives.

[Formula 10]

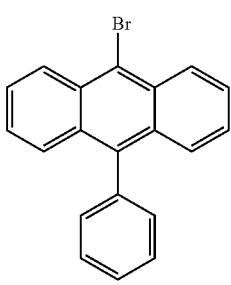

(100)

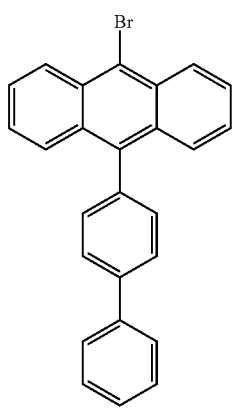

(101)

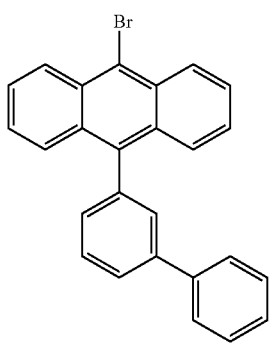

(102)

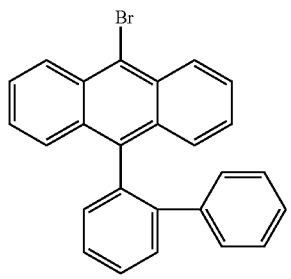

(103)

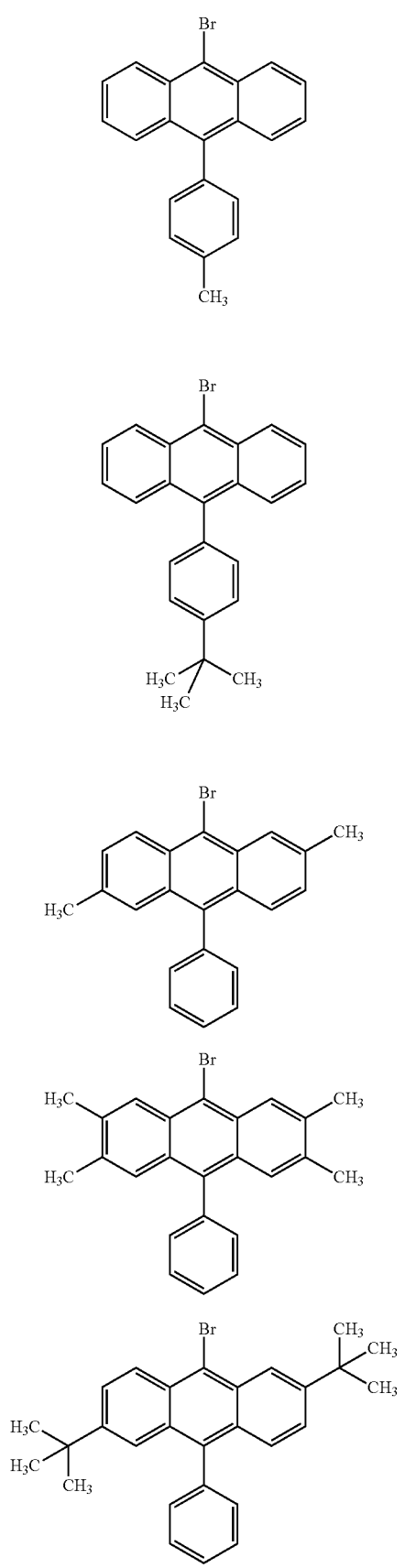

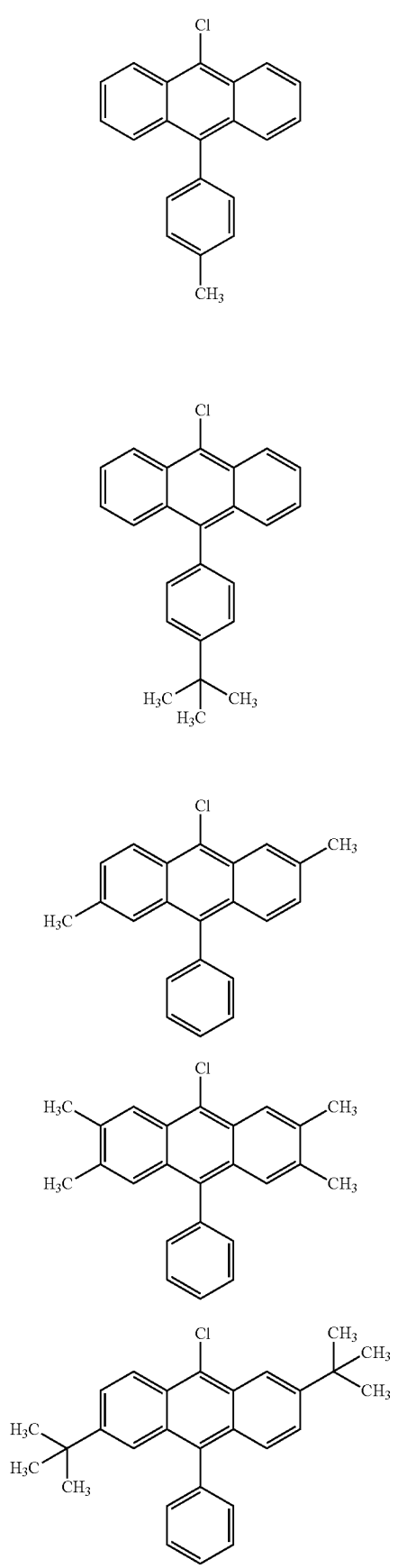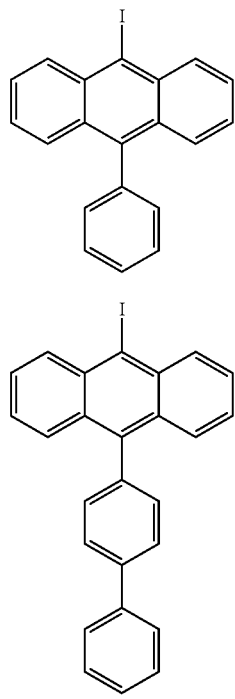

-continued

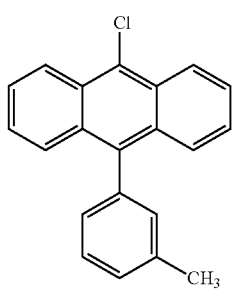
(123)

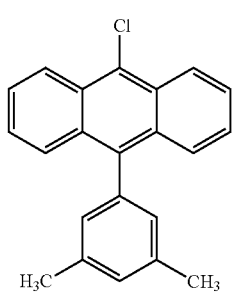
(124)

In addition, examples of the carbazole-3-yl-aryl derivative, which can be used for the method for synthesizing an anthracene derivative according to an aspect of the present invention, include carbazole derivatives represented by the general formula (c3). However, it is to be noted that the present invention is not limited to these carbazole derivatives.

[Formula 13]

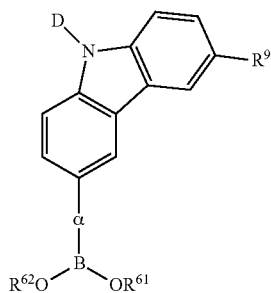
(c3)

In the general formula (c3), D represents any of an alkyl group having 1 to 4 carbon atoms and a substituted or unsubstituted phenyl group. In addition, a represents any of a substituted or unsubstituted phenylene group and a substituted or unsubstituted biphenyl-4,4'-diyl group. In addition, $R^9$ represents any of hydrogen, an alkyl group having 1 to 4 carbon atoms, and a substituted or unsubstituted phenyl group. In addition, $R^{61}$ and $R^{62}$ independently represent any of hydrogen and an alkyl group having 1 to 6 carbon atoms, and $R^{61}$ and $R^{62}$ may be bonded with each other to form a ring.

In addition, specific examples of the carbazole-3-yl-aryl derivative having an active site at a 10-position, represented by the general formula (c3), include carbazole derivatives represented by the structural formulae (200) to (218). However, it is to be noted that the present invention is not limited to these carbazole derivatives.

[Formula 14]

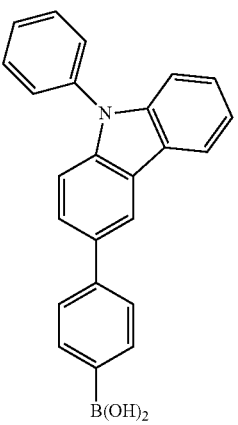
(200)

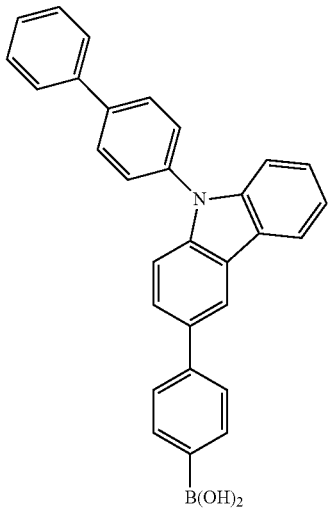
(201)

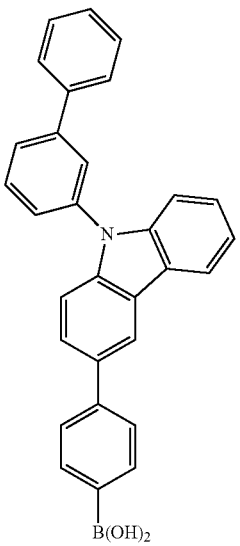
(202)

(203) 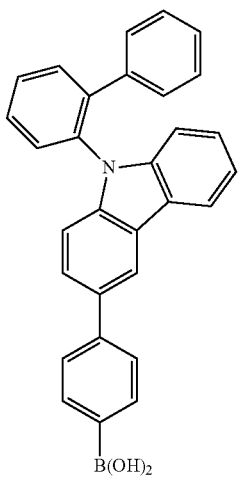
(204) 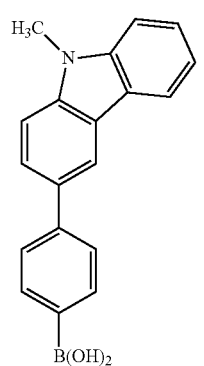
(205) 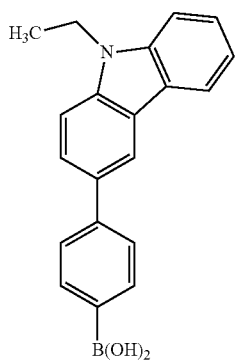
(206) 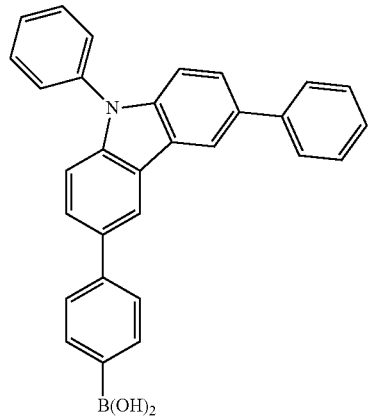
(207) 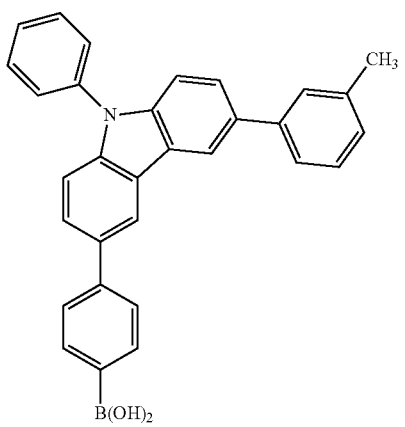
(208) 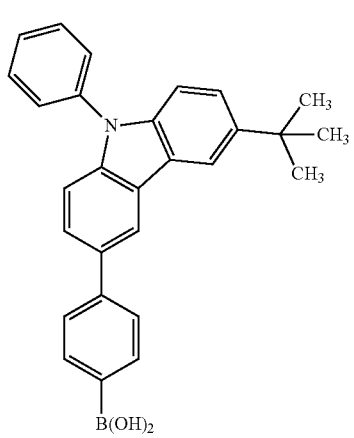
[Formula 15]
(209) 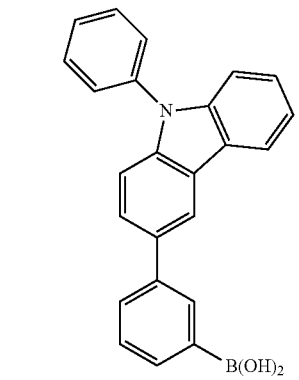

[Formula 16]
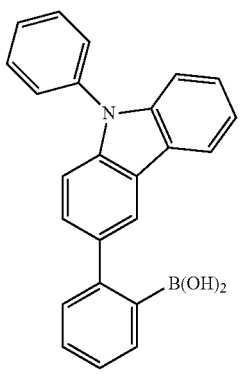
(210)
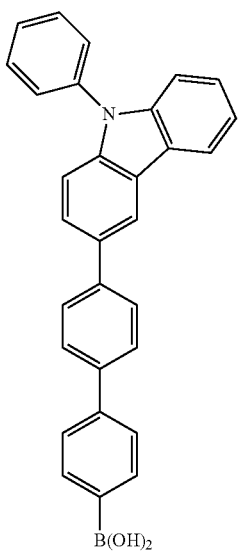
(211)
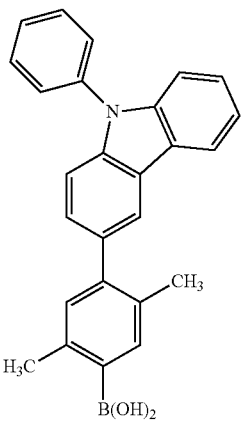
(212)
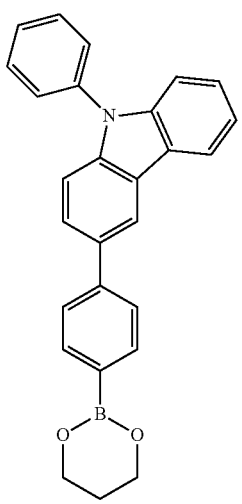
(213)
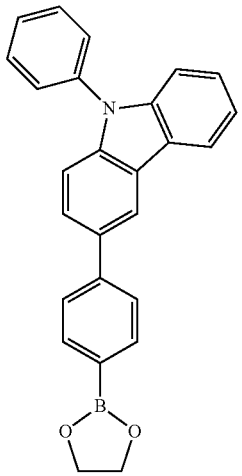
(214)
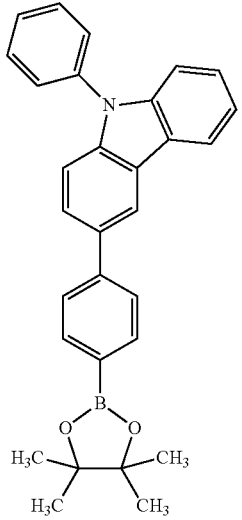
(215)

(216)

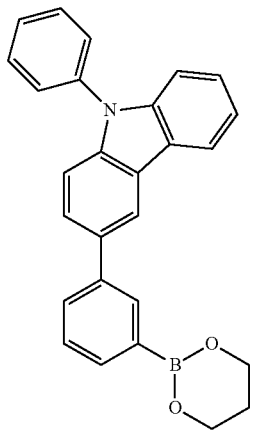

(217)

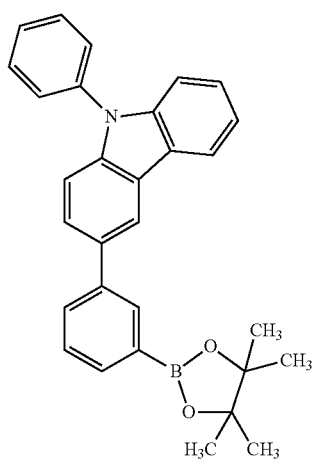

(218)

[Formula 17]

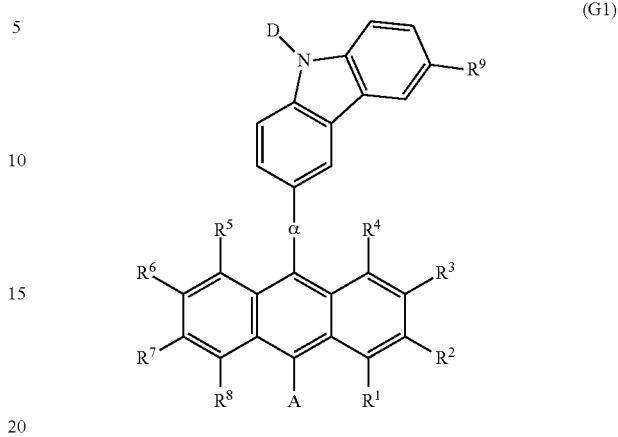

(G1)

In the general formula (G1), A represents a substituted or unsubstituted phenyl group. In addition, D represents any of an alkyl group having 1 to 4 carbon atoms and a substituted or unsubstituted phenyl group. In addition, a represents any of a substituted or unsubstituted phenylene group and a substituted or unsubstituted biphenyl-4,4'-diyl group. In addition, $R^1$ to $R^9$ independently represent any of hydrogen, an alkyl group having 1 to 4 carbon atoms, and a substituted or unsubstituted phenyl group.

In this embodiment, in Step 1, a carbazole-3-boron compound (c1) and a dihalogenated arene (b1) are subjected to a coupling reaction with the use of a metal catalyst to synthesize a 3-(halogenated aryl)-carbazole compound (c2). Then, in Step 2, a compound activated by reacting the 3-(halogenated aryl)-carbazole compound (c2) with a metal compound and a boron compound are reacted to synthesize a carbazole-3-aryl-boron compound (c3). Furthermore, in Step 3, the carbazole-3-aryl-boron compound (c3) and a 9-aryl-10-halogenated anthracene derivative (a1) are subjected to a coupling reaction with the use of a metal catalyst to obtain an anthracene derivative (G1) as an intended product.

(Step 1)

As shown in a synthetic scheme (A-1), the carbazole-3-boron compound (c1) and the dihalogenated arene (b1) are subjected to a coupling reaction with the use of a metal catalyst to obtain a 3-(halogenated aryl)-carbazole compound (c2).

[Formula 18]

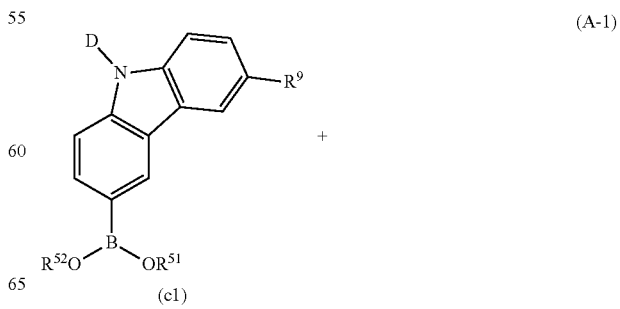

(A-1)

<21 Synthesis Method of Anthracene Derivative Represented by General Formula (G1)>

A method of synthesizing an anthracene derivative represented by the following general formula (G1) will be described.

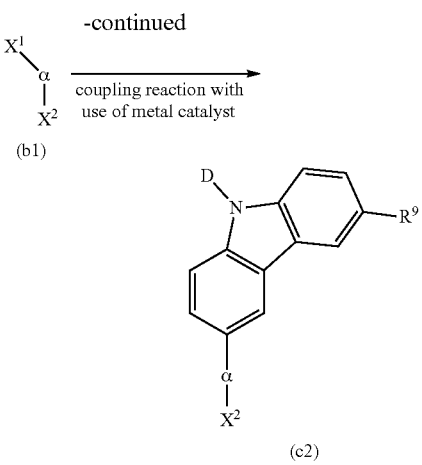

In the synthetic scheme (A-1), $X^1$ and $X^2$ independently represent halogen (chlorine, bromine, or iodine). In addition, $R^{51}$ and $R^{52}$ independently represent any of hydrogen and an alkyl group having 1 to 6 carbon atoms, and $R^{51}$ and $R^{52}$ may be bonded with each other to form a ring. In addition, D represents any of an alkyl group having 1 to 4 carbon atoms and a substituted or unsubstituted phenyl group. In addition, a represents any of a substituted or unsubstituted phenylene group and a substituted or unsubstituted biphenyl-4,4'-diyl group. In addition, $R^9$ represents any of hydrogen, an alkyl group having 1 to 4 carbon atoms, and a substituted or unsubstituted phenyl group.

In the case of carrying out the Suzuki-Miyaura coupling in the synthetic scheme (A-1), examples of a palladium catalyst that can be used include palladium (II) acetate, tetrakis(triphenylphosphine)palladium (0), and bis(triphenylphosphine) palladium (II) dichloride. In addition, examples of a ligand of the palladium catalyst which can be used include tri(ortho-tolyl)phosphine, triphenylphosphine, and tricyclohexylphosphine. In addition, examples of the base which can be used include organic bases such as sodium tert-butoxide, and inorganic bases such as a potassium carbonate and a sodium carbonate. Examples of the solvent that can be used include a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; and a mixed solvent of an ether such as ethylene glycol dimethyl ether and water. Furthermore, a mixed solvent of toluene and water; a mixed solvent of toluene, ethanol, and water; or a mixed solvent of ether such as ethylene glycol dimethyl ether and water is more preferable.

In the reaction shown in the synthetic scheme (A-1), cross coupling reactions may be used which employ organic aluminum, organic zirconium, organic zinc, organic zinc, and organic tin compounds, etc., besides the carbazole-3-boron compound (c1). Furthermore, in this coupling, a triflate group or the like may be used besides halogen.

In this case, $X^1$ and $X^2$ of the dihalogenated arene (b1) are independently halogen (chlorine, bromine, or iodine). In consideration of high reactivity, $X^1$ and $X^2$ are preferably bromine, and more preferably iodine. In order to selectively react the carbazole-3-boron compound (c1) with $X^1$ of the dihalogenated arene (b1), $X^1$ is preferably halogen with its reactivity higher than that of $X^2$ (for example, in the case of chlorine for $X^2$, $X^1$ is preferably bromine or iodine, whereas in the case of bromine for $X^2$, $X^1$ is preferably iodine).

In addition, a by-product (c2-2) produced by reacting one molecule of the dihalogenated arene (b1) with two molecules of the carbazole-3-boron compound (c1) has a much higher molecular weight than that of the intended 3-(halogenated aryl)-carbazole compound (c2), and can be thus easily separated by column purification.

In addition, this by-product (c2-2) has no active site, and thus will not react with other compounds in the subsequent reactions to produce any further by-products. Therefore, it is also possible to remove the compound (c1) with this by-product (c2-2) mixed after the subsequent reactions. For example, in a synthetic scheme (A-2) described later, a boronic acid compound (c3) is less likely to dissolve in a nonpolar solvent such as hexane, than the by-product (c2-2), and can be thus easily separated by recrystallization. In addition, after synthesizing an anthracene derivative (G1) as an intended final product in accordance with a reaction scheme (A-3), the anthracene derivative (G1) may be purified in the removal of other impurities together to remove the by-product (c2-2).

[Formula 19]

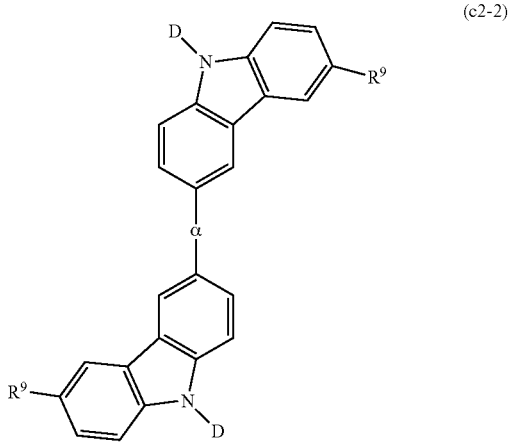

(Step 2)

As shown in the synthetic scheme (A-2), a compound activated by reacting the 3-(halogenated aryl)-carbazole compound (c2) with a metal or metal compound and a boron compound are reacted to synthesize a carbazole-3-aryl-boron compound (c3).

[Formula 20]

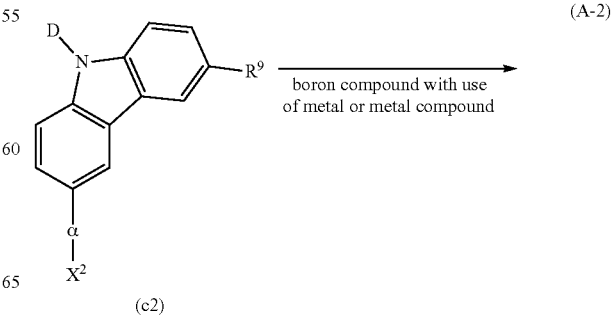

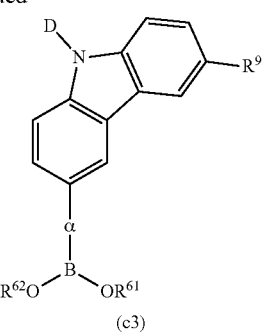

(c3)

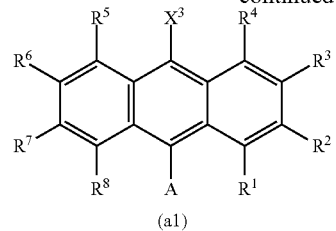

(a1)

coupling reaction with use of metal catalyst

In the synthetic scheme (A-2), D represents any of an alkyl group having 1 to 4 carbon atoms and a substituted or unsubstituted phenyl group. In addition, a represents any of a substituted or unsubstituted phenylene group and a substituted or unsubstituted biphenyl-4,4'-diyl group. In addition, $R^9$ represents any of hydrogen, an alkyl group having 1 to 4 carbon atoms, and a substituted or unsubstituted phenyl group. In addition, $R^{61}$ and $R^{62}$ independently represent any of hydrogen and an alkyl group having 1 to 6 carbon atoms, and $R^{61}$ and $R^{62}$ may be bonded with each other to form a ring. In addition, $X^2$ represents halogen (chlorine, bromine, or iodine).

As one example of the activation, a lithiation reaction can be used with an alkyl lithium reagent as the metal compound. Examples of the alkyl lithium reagent include n-butyllithium, tert-butyllithium, and methyllithium. Examples of the boron compounds include trimethyl borate, triethyl borate, and isopropoxyl pinacol borane. As the solvent, dehydrated solvents can be used, for example, ethers such as diethyl ethers and tetrahydrofuran (THF), etc.

As for the metal for the activation, a reaction can be used with activated magnesium for a Grignard reagent. For the activation of magnesium, iodine and 1,2-dibromoethane can be used.

(Step 3)

As shown in the synthetic scheme (A-3), the carbazole-3-aryl-boron compound (c3) and the 9-aryl-10-halogenated anthracene derivative (a1) are subjected to a coupling reaction with the use of a metal catalyst to obtain an anthracene derivative (G1) as an intended product.

[Formula 21]

(A-3)

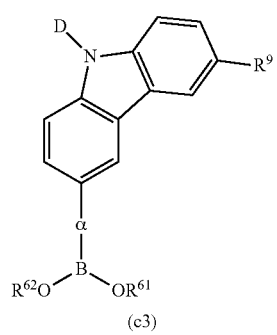

(c3)

+

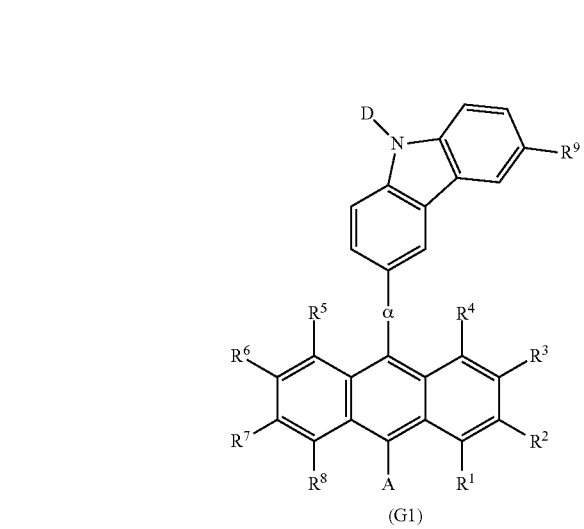

(G1)

In the synthetic scheme (A-3), $X^3$ represents halogen (chlorine, bromine, or iodine). In consideration of high reactivity, $X^3$ is preferably bromine, and more preferably iodine. In addition, D represents any of an alkyl group having 1 to 4 carbon atoms and a substituted or unsubstituted phenyl group. In addition, a represents any of a substituted or unsubstituted phenylene group and a substituted or unsubstituted biphenyl-4,4'-diyl group. In addition, A represents a substituted or unsubstituted phenyl group. In addition, $R^1$ to $R^9$ independently represent any of hydrogen, an alkyl group having 1 to 4 carbon atoms, and a substituted or unsubstituted phenyl group. In addition, $R^{61}$ and $R^{62}$ independently represent any of hydrogen and an alkyl group having 1 to 6 carbon atoms, and $R^{61}$ and $R^{62}$ may be bonded with each other to form a ring.

In the synthetic scheme (A-3), the Suzuki-Miyaura coupling may be used as in the case of the synthetic scheme (A-1).

The method for synthesizing the anthracene derivative (G1) synthesized describe above according to the embodiment is a synthesis method in which by-products are less likely to be synthesized and if any by-products are produced, the by-products are easily removed. In addition, as compared with conventional synthesis methods, the method is a simpler synthetic method including fewer synthetic steps. Therefore, the intended product can be synthesized with a higher degree of purity.

Example 1

In this Example, a method for synthesizing 9-phenyl-3-[4-(10-phenyl-9-anthryl)phenyl]-9H-carbazole (abbreviation: PCzPA) represented by the following structural formula (P1) will be described.

[Formula 22]

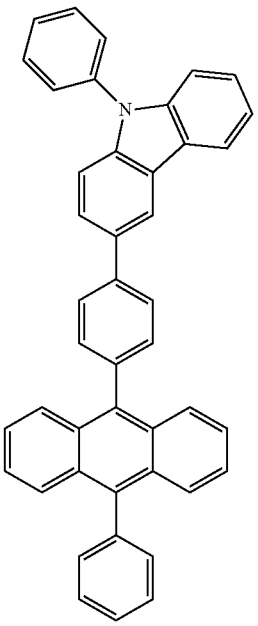

(P1)

Step 1: Synthesis Method of 3-(4-bromophenyl)-9-phenyl-9H-carbazole

A synthesis scheme for 3-(4-bromophenyl)-9-phenyl-9H-carbazole is illustrated in the following (F-1).

[Formula 23]

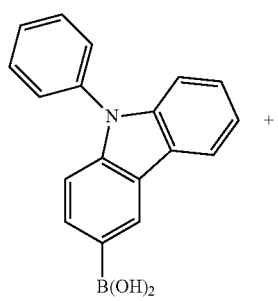

+

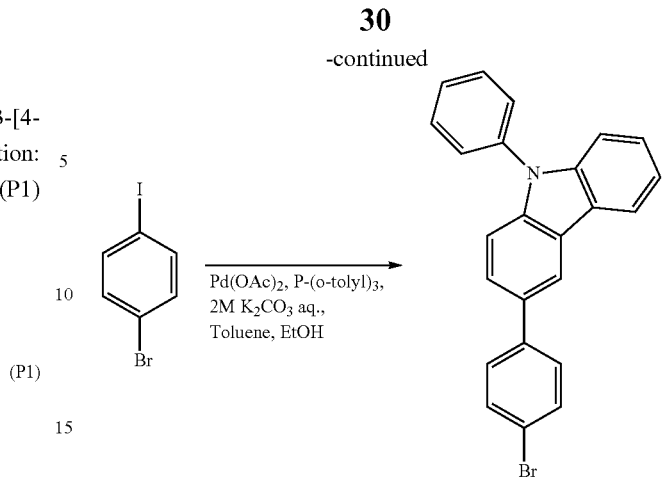

(F-1)

In a 300-mL three-neck flask, a mixture of 14 g (50 mmol) of 4-bromoiodobenzene, 14 g (50 mmol) of 9-phenyl-9H-carbazol-3-boronic acid, 110 mg (0.5 mmol) of palladium (II) acetate, 300 mg (10 mmol) of tri(o-tolyl) phosphine, 50 mL of toluene, 10 mL of ethanol, and 25 mL of a potassium carbonate aqueous solution (2 mol/L) was degassed while being stirred under reduced pressure, and reacted while being heated and stirred under a nitrogen atmosphere at 80° C. for 6 hours.

After the reaction, 200 mL of toluene was added to the reaction mixture solution, and the resulting suspension was filtrated through Florisil (produced by Wako Pure Chemical Industries, Ltd., Catalog No. 540-00135) and Celite (produced by Wako Pure Chemical Industries, Ltd., Catalog No. 531-16855). The obtained filtrate was washed with water, and magnesium sulfate was added thereto to adsorb moisture. This suspension was filtrated to obtain a filtrate. The obtained filtrate was concentrated, and purified by silica gel column chromatography. In this case, a mixed solvent of toluene and hexane (toluene: hexane=1:4) was used as a developing solvent for the chromatography. The obtained fraction was concentrated, and hexane was added thereto. The mixture was exposed to ultrasonic waves and then recrystallized to obtain a white powder as an intended product with a yield of 15 g at 75%.

The Rf value of the intended product obtained by silica gel thin layer chromatography (TLC) (developing solvent, ethyl acetate:hexane=1:10) was 0.32 and the Rf value of the 4-bromoiodobenzene was 0.74.

In addition, while an Rf value of the 1,4-bis(9-phenyl-9H-carbazol-3-yl)benzene, which was a by-product, (developing solvent, ethyl acetate:hexane=1:10) was 0.23, spots were slightly observed on the TLC in the reaction suspension. As a result, it was determined that since the iodine moiety had higher reactivity than that of the bromo moiety in 4-bromoiodobenzene which was a dihalide and was used for the raw material, the 4-bromoiodobenzene was selectively (preferentially) reacted with the 9-phenyl-9H-carbazol-3-boronic acid which was a boron compound (that is, the dihalide and the boron compound was able to be reacted almost at 1:1). Furthermore, since the Rf value of the intended product is sufficiently far from the Rf value of the by-product, the intended product and the by-product was able be easily separated in the column purification.

The compound obtained in Step 1 described above was measured by a nuclear magnetic resonance (NMR) method. The measurement data is shown below.

$^1$H-NMR (CDCl$_3$, 300 MHz): δ (ppm)=7.24-7.32 (m, 1H), 7.40-7.64 (m, 13H), 8.17 (d, J=7.2, 1H), and 8.29 (s, 1H).

Figure 1B:
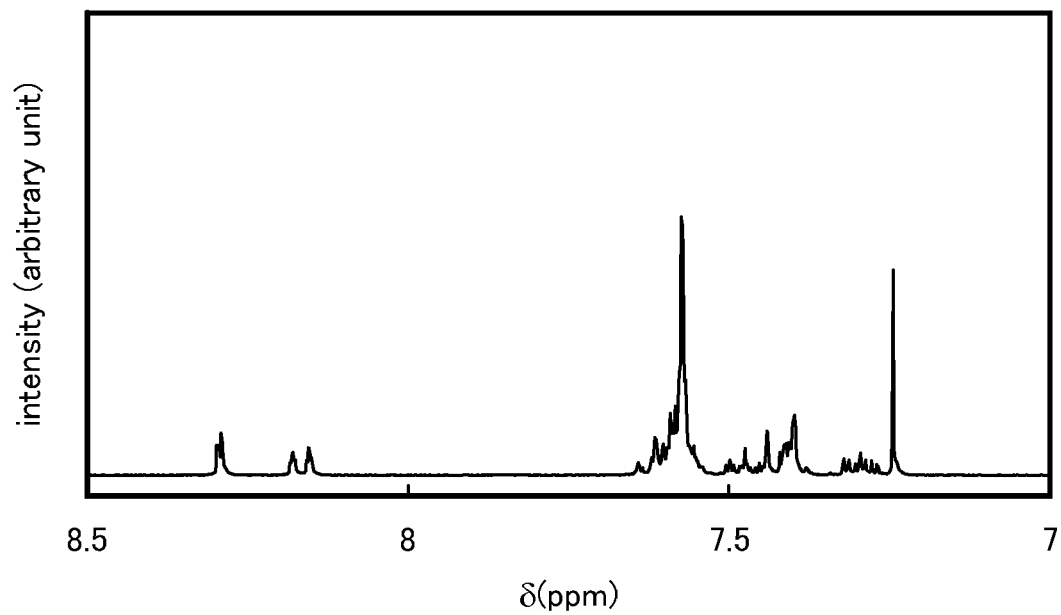

In addition, the ¹H-NMR charts are shown in FIGS. 1A and 1B. It is to be noted that FIG. 1B is a chart representing an enlargement of FIG. 1A in a range of from 7.0 to 8.5 ppm. It was confirmed from the measurement results that 3-(4-bromophenyl)-9-phenyl-9H-carbazole, which was the intended product, was obtained.

Figure 2:
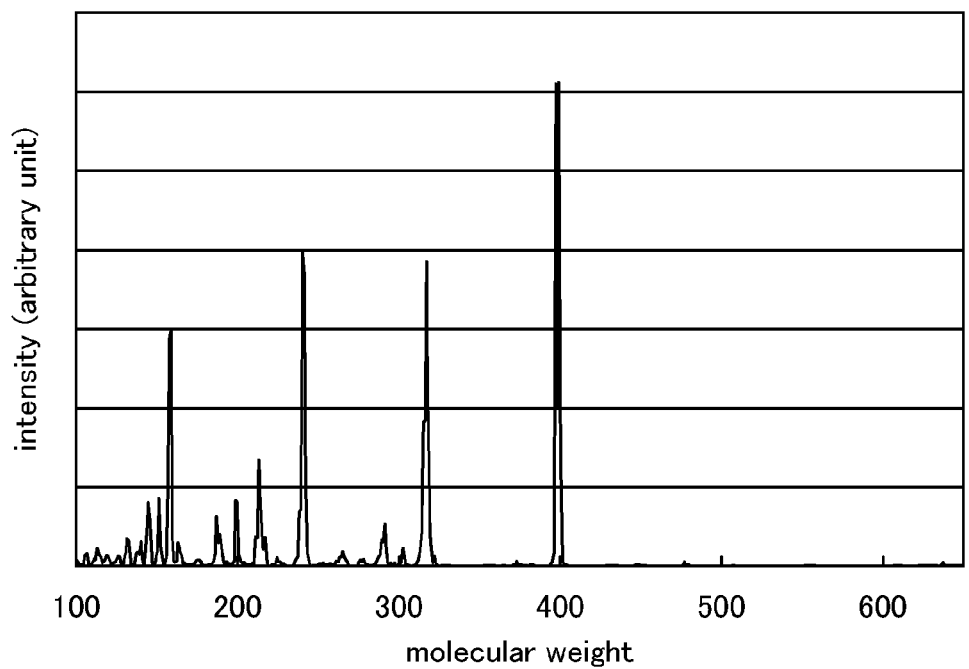
FIG. 2 is a diagram showing a GC-MS chart for 3-(4-bromophenyl)-9-phenyl-9H-carbazol.

The molecular weight of the above compound was measured by a GC-MS detector (ITQ1100 ion trap GC/MS system, manufactured by Thermo Fisher Scientific K.K.). The chart is shown in FIG. 2. The measurement detected a main peak at a molecular weight of 397.13 (the mode was EI+), and it was thus confirmed from the measurement result that 3-(4-bromophenyl)-9-phenyl-9H-carbazole, which was the intended product, was obtained.

In addition, any peak derived from 1,4-bis(9-phenyl-9-H-carbazol-3-yl)benzene (molecular weight: 560.2), which was a by-product, was not detected by this GC-MS detection. Therefore, it is determined that the implementation of the reaction in Step 1 provided the intended product with a higher degree of purity in a simple manner with an extremely high yield.

Step 2: Synthesis Method of
4-(9-phenyl-9-H-carbazol-3-yl)phenylboronic acid

A synthetic scheme for 4-(9-phenyl-9-H-carbazol-3-yl)phenylboronic acid is illustrated in the following (F-2).

[Formula 24]

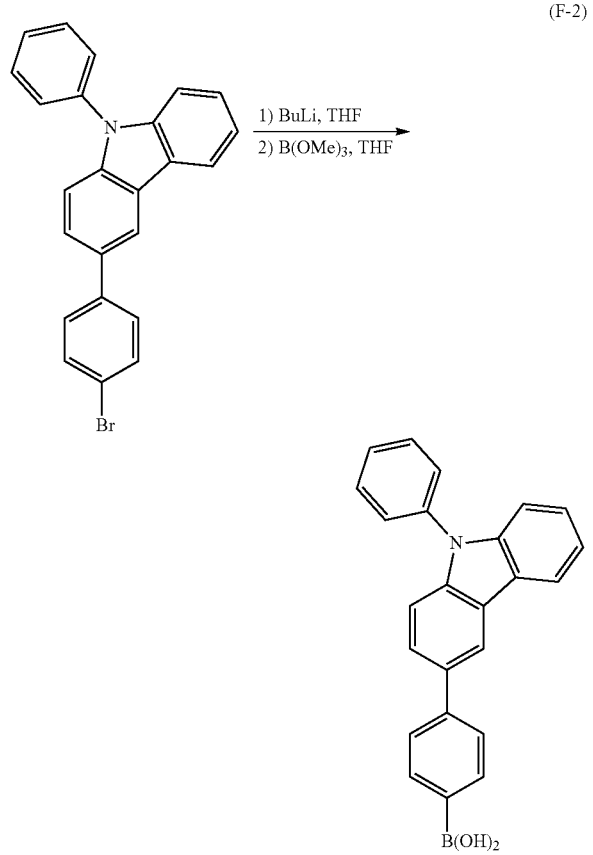

(F-2)

Into a 300-mL three-neck flask, 8.0 g (20 mmol) of the 3-(4-bromophenyl)-9-phenyl-9H-carbazole obtained in Step 1 described above was put, the atmosphere in the flask was replaced with nitrogen, 100 mL of dehydrated tetrahydrofuran (abbreviation: THF) was then added to the flask, and the temperature was lowered to −78° C. Into this mixture solution, 15 mL (24 mmol) of a 1.65 mol/L n-butyllithium hexane solution was dropped, and the mixture solution with the n-butyllithium hexane solution added was stirred for 2 hours. To this mixture, 3.4 mL (30 mmol) of trimethyl borate was added, and the mixture with the trimethyl borate added was stirred at −78° C. for 2 hours and at room temperature for 18 hours. After the reaction, 1M diluted hydrochloric acid was added to this reaction solution until the solution became acid, and the solution with the diluted hydrochloric acid added was stirred for 7 hours. This solution was subjected to ethyl acetate extraction, and the obtained organic layer was washed with a saturated saline. After the washing, magnesium sulfate was added to the organic layer to adsorb moisture. This suspension was filtrated, and the obtained filtrate was concentrated, and hexane was added thereto. The mixture was exposed to supersonic waves and then recrystallized to obtain an intended white powder with a yield of 6.4 g at 88%.

The Rf value of the intended product obtained by silica gel thin layer chromatography (TLC) (developing solvent, ethyl acetate:hexane=1:10) was 0 (origin), and the Rf value of the 3-(4-bromophenyl)-9-phenyl-9H-carbazole was 0.53. In addition, the Rf value of the intended product obtained by silica gel thin layer chromatography (TLC) using ethyl acetate as the developing solvent was 0.72, and the Rf value of the 3-(4-bromophenyl)-9-phenyl-9H-carbazole was 0.93. In any case of the developing solvents, no spot derived from the 3-(4-bromophenyl)-9-phenyl-9H-carbazole was observed. Therefore, it is determined that the implementation of the reaction in Step 2 provided the intended product with a higher degree of purity in a simple manner with an extremely high yield.

In Step 2, the 3-(4-bromophenyl)-9-phenyl-9H-carbazole as a raw material halide was reacted with n-butyllithium whose amount (1.2 equivalents) is larger than that of the 3-(4-bromophenyl)-9-phenyl-9H-carbazole as a lithiating agent so that the raw material halide was not left. In addition, the raw material halide is more likely to dissolve in a nonpolar solvent such as hexane, than the boron compound (4-(9-phenyl-9-H-carbazol-3-yl)phenylboronic acid) as the intended product, and can be thus easily separated by recrystallization. This allows for preventing an impurity from being produced by a coupling reaction between the boron compound (4-(9-phenyl-9-H-carbazol-3-yl)phenylboronic acid) synthesized in Step 2 and a halide (3-(4-bromophenyl)-9-phenyl-9H-carbazole), which was an impurity in the boron compound, in the next step of a reaction with a halogenated anthracene compound.

Step 3: Synthesis Method of 9-phenyl-3-[4-(10-phenyl-9-anthryl)phenyl]-9H-carbazole (abbreviation: PCzPA)

A synthetic scheme for 9-phenyl-3-[4-(10-phenyl-9-anthryl)phenyl]-9H-carbazole (abbreviation: PCzPA) is illustrated in the following (F-3).

[Formula 25]

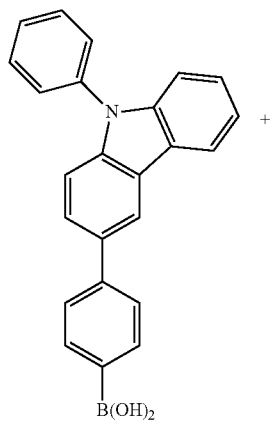

+

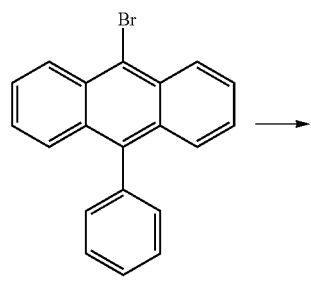

→

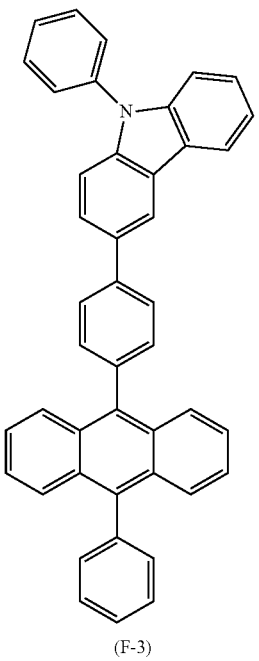

(F-3)

The reaction between 9-bromo-10-phenylantracene and the 4-(9-phenyl-9-H-carbazol-3-yl)phenylboronic acid was carried out in accordance with a Suzuki coupling method (by heating and stirring in an organic solvent with the use of a palladium catalyst, a ligand of the palladium catalyst, and a base).

After the reaction, this reaction mixture solution was purified to obtain a pale yellow powder as the indented product.

The compound obtained in Step 3 described above was measured by a nuclear magnetic resonance (NMR) method. The measurement data is shown below.

$^1$H-NMR (CDCl$_3$, 300 MHz): δ (ppm)=7.26-7.74 (m, 22H), 7.83-7.89 (m, 3H), 7.97 (d, J=7.8 Hz, 2H), 8.25 (d, J=5.2 Hz, 1H), and 8.55 (d, J=1.5 Hz, 1H).

Figure 3A:
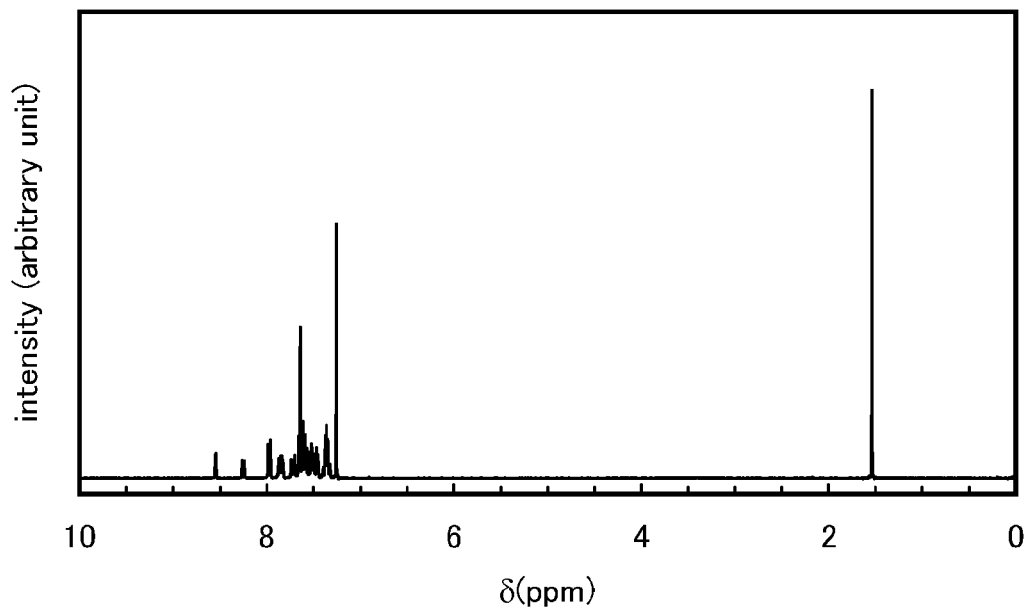
FIGS. 3A and 3B diagrams showing $^1$H NMR charts for 9-phenyl-3-[4-(10-phenyl-9-anthryl)phenyl]-9H-carbazole.
Figure 3B:
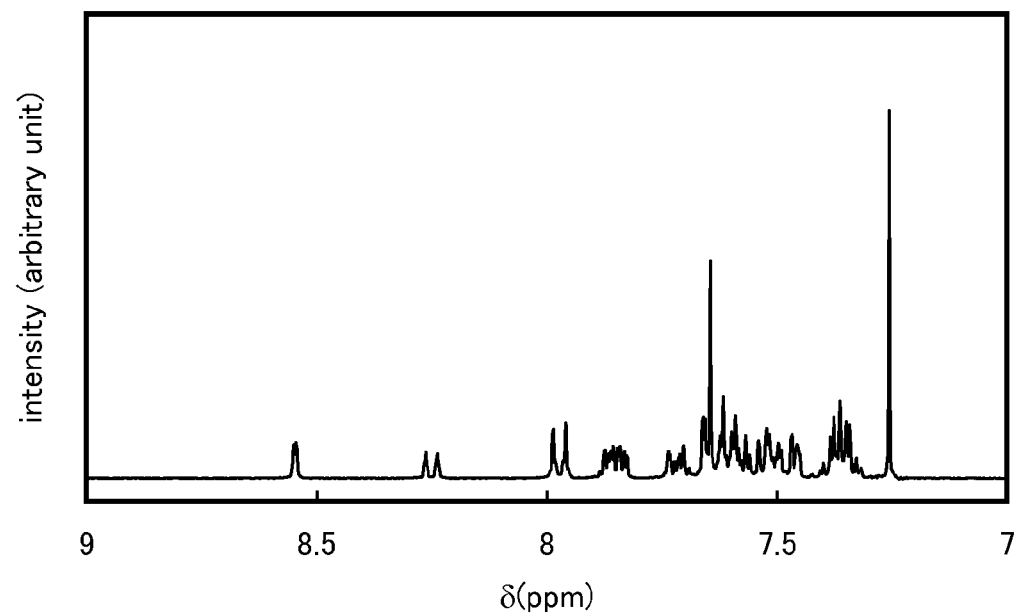

In addition, the $^1$H-NMR charts are shown in FIGS. 3A and 3B. It is to be noted that FIG. 3B is a chart representing an enlargement of FIG. 3A in the range of 7.0 ppm to 9.0 ppm. It was confirmed from the measurement result that PCzPA, which was the intended product, was obtained.

The compound obtained in Step 3 was evaluated for its glass transition temperature with the use of a differential scanning calorimeter (DSC). According to the measurement result, the glass transition temperature was 215° C. In addition, the melting point was 267° C. As described above, it has been determined that the PCzPA obtained by employing the method for synthesizing an anthracene derivative according to an aspect of the present invention exhibits a high glass transition temperature and has a favorable heat resistance. In addition, the PCzPA has no peak indicating crystallization, and it has been thus determined that the PCzPA is a substance which is less likely to be crystallized.

It has been determined from the results described above that the method for synthesizing an anthracene derivative according to an aspect of the present invention can synthesize an anthracene derivative with a high degree of purity in a pretty simple manner.

This application is based on Japanese Patent Application serial no. 2010-003487 filed with Japan Patent Office on Jan. 11, 2010, the entire contents of which are hereby incorporated by reference.

What is claimed is:

1. A method for synthesizing an anthracene derivative represented by a general formula (G1), in which a 9-arylanthracene derivative having an active site at a 10-position is subjected to coupling with a (9-aryl-9H-carbazol-3-yl)aryl boronic acid with the use of a metal or a metal compound,

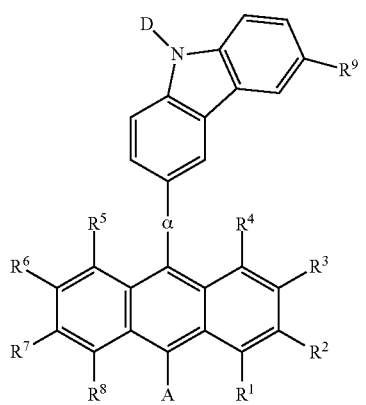

(G1)

wherein A represents a substituted or unsubstituted phenyl group, wherein D represents any of an alkyl group having 1 to 4 carbon atoms and a substituted or unsubstituted phenyl group, wherein α represents any of a substituted or unsubstituted phenylene group and a substituted or unsubstituted biphenyl-4,4'-diyl group, and wherein R¹ to R⁹ independently represent any of hydrogen, an alkyl group having 1 to 4 carbon atoms, and a substituted or unsubstituted phenyl group.

2. The method for synthesizing an anthracene derivative according to claim 1, wherein one of the active sites is halogen, whereas the other of the active sites is a boronic acid or organoboron.

3. The method for synthesizing an anthracene derivative according to claim 1, wherein a palladium compound is used for the metal compound.

4. A method for synthesizing an anthracene derivative represented by a general formula (G1), in which a 9-aryl-10-halogenated anthracene is subjected to coupling with a (9-aryl-9H-carbazol-3-yl)aryl boronic acid with the use of a metal compound,

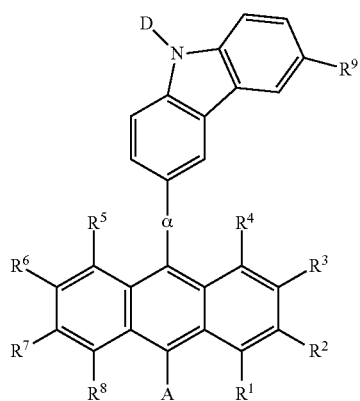

(G1)

wherein A represents a substituted or unsubstituted phenyl group, wherein D represents any of an alkyl group having 1 to 4 carbon atoms and a substituted or unsubstituted phenyl group, wherein α represents any of a substituted or unsubstituted phenylene group and a substituted or unsubstituted biphenyl-4,4'-diyl group, and wherein R¹ to R⁹ independently represent any of hydrogen, an alkyl group having 1 to 4 carbon atoms, and a substituted or unsubstituted phenyl group.

5. The method for synthesizing an anthracene derivative according to claim 4, wherein a palladium compound is used for the metal compound.

6. A method for synthesizing an anthracene derivative represented by a general formula (G1), in which the anthracene derivative represented by a general formula (a1) is subjected to coupling with a carbazole derivative represented by a general formula (c3) with the use of a metal or a metal compound,

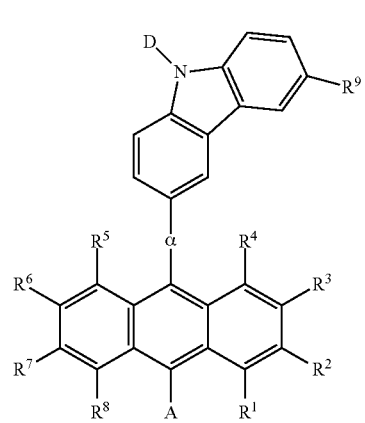

(G1)

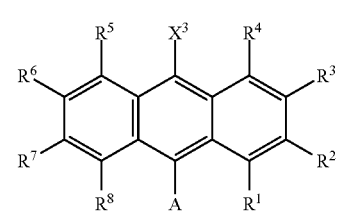

(a1)

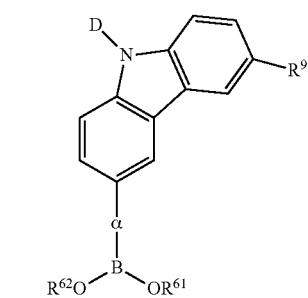

(c3)

wherein A represents a substituted or unsubstituted phenyl group, wherein D represents any of an alkyl group having 1 to 4 carbon atoms and a substituted or unsubstituted phenyl group, wherein α represents any of a substituted or unsubstituted phenylene group and a substituted or unsubstituted biphenyl-4,4'-diyl group, wherein R¹ to R⁹ independently represent any of hydrogen, an alkyl group having 1 to 4 carbon atoms, and a substituted or unsubstituted phenyl group, wherein X³ represents any of chlorine, bromine, and iodine, and wherein R⁶¹ and R⁶² independently represent any of hydrogen and an alkyl group having 1 to 6 carbon atoms, and R⁶¹ and R⁶² may be bonded with each other to form a ring.

7. The method for synthesizing an anthracene derivative according to claim 6, wherein a palladium compound is used for the metal compound.

8. A method for synthesizing an anthracene derivative represented by a structural formula (P1), in which the anthracene derivative represented by a structural formula (S1) is subjected to coupling with a carbazole derivative represented by a structural formula (S2) with the use of a metal or a metal compound,

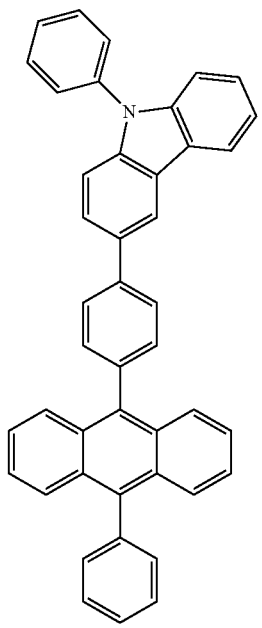 (P1)

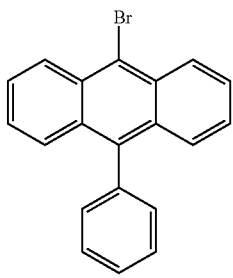 (S1)

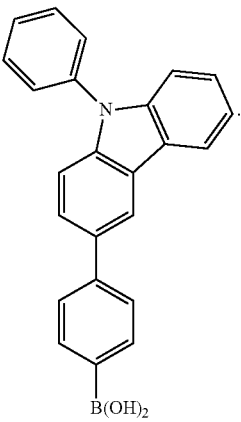 (S2)

9. The method for synthesizing an anthracene derivative according to claim 8, wherein a palladium compound is used for the metal compound.

* * * * *